United States Patent [19]

Tilstam et al.

[11] Patent Number: 5,386,028
[45] Date of Patent: Jan. 31, 1995

[54] PROCESS FOR THE PRODUCTION OF N-β-HYDROXYALKYL-TRI-N-CARBOXYALKYL-1,4,7,10-TETRAAZACYCLODODECANE AND N-β-HYDROXYALKYL-TRI-N-CARBOXYALKYL-1,4,8,11-TETRAAZACYCLOTETRADECANE DERIVATIVES AND THEIR METAL COMPLEXES

[75] Inventors: Ulf Tilstam; Helmut Börner; Klaus Nickisch; Heinz Gries; Johannes Platzek, all of Berlin, Germany

[73] Assignee: Schering Aktiengesellschaft, Berlin and Bergkamen, Germany

[21] Appl. No.: 16,452

[22] Filed: Feb. 11, 1993

Related U.S. Application Data

[63] Continuation of Ser. No. 987,468, Dec. 7, 1992, abandoned.

[30] Foreign Application Priority Data

Jun. 4, 1992 [DE] Germany .............................. 4218744

[51] Int. Cl.$^6$ ..................... C07D 257/02; C08F 4/64; A61K 49/02
[52] U.S. Cl. .................................. 540/474; 540/452; 429/9
[58] Field of Search ................. 540/452, 474

[56] References Cited

U.S. PATENT DOCUMENTS

| | | | |
|---|---|---|---|
| 4,085,106 | 4/1978 | Atkins .................................. | 540/474 |
| 4,130,715 | 12/1978 | Atkins .................................. | 540/474 |
| 4,937,333 | 6/1990 | Garlich et al. ......................... | 540/474 |
| 4,994,560 | 2/1991 | Kruper, Jr. et al. .................. | 540/474 |
| 5,006,643 | 4/1991 | Fazio et al. ........................... | 540/452 |
| 5,053,503 | 10/1991 | Dean et al. ............................ | 540/474 |
| 5,064,802 | 11/1991 | Stevens et al. ....................... | 502/155 |
| 5,064,956 | 11/1991 | Kruper, Jr. ............................ | 540/474 |

FOREIGN PATENT DOCUMENTS

| | | | |
|---|---|---|---|
| 0296522 | 12/1988 | European Pat. Off. ............ | 540/474 |
| 0353450 | 2/1990 | European Pat. Off. ............ | 540/474 |
| 0367223 | 5/1990 | European Pat. Off. ............ | 562/561 |
| 0374929 | 6/1990 | European Pat. Off. ............ | 540/474 |
| 0374947 | 6/1990 | European Pat. Off. ............ | 540/474 |
| 0411941 | 2/1991 | European Pat. Off. ............ | 540/474 |
| 0448191 | 9/1991 | European Pat. Off. ............ | 540/474 |
| 0462787 | 12/1991 | European Pat. Off. ............ | 540/474 |
| 0468634 | 1/1992 | European Pat. Off. ............ | 540/474 |
| 0485045 | 5/1992 | European Pat. Off. ............ | 540/474 |
| 89/12631 | 12/1989 | WIPO ................................. | 540/474 |
| 92/04336 | 3/1992 | WIPO ................................. | 540/474 |

Primary Examiner—Robert T. Bond
Attorney, Agent, or Firm—Millen, White, Zelano, & Branigan

[57] ABSTRACT

A process for the production of N-β-hydroxyalkyl-tri-N-carboxyalkyl-1,4,7,10-tetraazacyclododecane and N-β-hydroxyalkyl-tri-N-carboxyalkyl-1,4,8,11-tetraazacyclotetradecane derivatives and their metal complexes is described.

16 Claims, No Drawings

PROCESS FOR THE PRODUCTION OF N-β-HYDROXYALKYL-TRI-N-CARBOXYALKYL-1,4,7,10-TETRAAZACYCLODODECANE AND N-β-HYDROXYALKYL-TRI-N-CARBOXYALKYL-1,4,8,11-TETRAAZACYCLOTETRADECANE DERIVATIVES AND THEIR METAL COMPLEXES

This is a continuation of application Ser. No. 07/987,468 Dec. 7, 1992, now abandoned.

BACKGROUND OF THE INVENTION

The invention relates to a process for the production of N-β-hydroxyalkyl-tri-N-carboxyalkyl-1,4,7,10-tetraazacyclododecane and N-β-hydroxyalkyl-tri-N-carboxyalkyl-1,4,8,11-tetraazacyclotetradecane derivatives and their metal complexes.

Because of their importance for the production of imaging diagnostic agents (DE OS 36 25 417), especially NMR diagnostic agents, the production of N-β-hydroxyalkyl-tri-N-carboxyalkyl-1,4,7,10-tetraazacyclododecane and N-β-hydroxyalkyl-tri-N-carboxyalkyl-1,4,8,11-tetraazacyclotetradecane derivatives has been tried in the many various ways without finding a satisfactory method of synthesis, especially for production on an industrial scale.

For the synthesis of tetraazamacrocycles (1,4,7,10-tetraazacyclododecane derivatives or 1,4,8,11-tetraazacyclotetradecane derivatives) with the above-mentioned substitution pattern, basically three different methods are followed in the prior art:

1) A start is made from two reactants, which are cyclized to the tetraazamacrocycle according to methods known in the literature [e.g., Richman, Org. Synthesis 58, 86 (1978); Atkins, J. Amer. Chem. Soc. 96, 2268 (1974)]. One of the two reactants contains a protected nitrogen atom and carries on the chain end two leaving groups (e.g., bromine, mesyloxy, tosyloxy, triflate or alkoxycarbonyl groups), which are nucleophilically displaced from the terminal nitrogen atoms of the second reactant, a protected triaza compound whose protecting groups are distinguished from the protecting group of the first reactant. A tetrasubstituted tetraazamacrocycle with three identical protecting groups and one protecting group different therefrom is thus obtained. The protecting groups can be specifically cleaved and the desired substituents are introduced. As an example, the reaction of the disodium salt of N,N',N''-tris(p-tolylsulfonyl)diethylenetriamine [Ciampolini, J. Chem. Soc. Chem. Commun. 998 (1984)] with N-bis-(2-methanesulfonyloxyethyl)triphenylmethylamine in dimethylformamide at 80°-150° C. with subsequent cleavage of the trityl group under acidic conditions can be mentioned. The yields of both reaction stages are generally poor. After the subsequent specific monosubstitution for the introduction of substituent $R^2$ [Ciampolini, J. Chem. Soc. Chem. Commun. 998 (1984); Kaden, Helv. Chim. [Swiss Chem.] Acta 66, 861 (1983); Basefield, Inorg. Chem. 25, 4663 (1986)], the protecting groups are removed on three nitrogen atoms, e.g., by alkali metal in ammonia [Helv. Chim. Acta, ,56, 2216 (1973); Helv. Chim. Acta 59, 1566 (1976); J. Org. Chem. 53, 3521 (1988)], lithium aluminum hydride [F. Vögle, Liebigs Ann. Chem. 1344 (1977)], Red.-Al ® [E. H. Gold, J. Org. Chem. 37, 2208, (1972)], Na—Hg [M. Kellog, J. Org. Chem. 49, 110 (1984)], electrolysis [M. Hesse, Helv. Chim. Acta 71 (1988), 7, 1708] or hydrobromic acid/phenol/glacial acetic acid [N. G. Lukyanenko, Synthesis, 1988, 355]. Subsequent trialkylation with haloacetic acid derivatives finally results in a tetrasubstituted tetraazamacrocycle. The above-indicated processes of the protecting group cleavage are generally connected with poor yields, limits on the batch size with respect to the amount of reagent to be used (e.g., in the sodium-amalgam method) and above all cannot be used in the case of substituents which carry sensitive groups (e.g., hydroxyalkyl).

2) By statistical trisubstitution of the unprotected tetraazamacrocycle, a tetraazamacrocycle substituted with three identical radicals (e.g., tosyl, benzoyl, carboxyethyl radical) is obtained in another process. Monosubstituted and disubstituted products also result, which have to be separated by selective precipitation, chromatography and crystallization (EP 232 751, EP 292 689). In both European patent applications, a yield of about 23% is obtained in the stage of the statistical trisubstitution. This means that 77% of the very expensive starting material 1,4,7,10tetraazacyclododecane is lost. The subsequent stages can then follow as already described under 1). All drawbacks of a statistical reaction known to one skilled in the art, such as the above-indicated low yields and separation problems (above all in the production of substantial amounts of substances) make this process appear to be nonadvantageous.

3) Tweedle et al. describe in European patent application 292 689 that starting from the unsubstituted macrocyclic compound 1,4,7,10-tetraazacyclododecane, the N-formyl compound can be obtained by a tricyclic intermediate stage. This compound still carrying three unprotected nitrogen atoms can now be trialkylated, deformylated and converted to the tetrasubstituted tetraazamacrocycle with haloacetic ester derivatives. But the number of reaction steps to the tris-carboxymethyl-monoalkyl-tetraazamacrocycle is also highly unsatisfactory in this process. Also, it has been shown that the tricyclic intermediate stage is extremely sensitive toward water, alcohol and dimethylformamide. These substances cannot be removed completely enough in large batches, which leads to yield losses, which jeopardize the usability of the process on an industrial scale.

Thus, it has not been possible to find a satisfactory synthesis method for the desired tetrasubstituted tetraazamacrocycles, which are to be considered as key compounds for the tri-N-carboxyalkyl-metal complexes being used, e.g., as valuable NMR and x-ray contrast media.

Because of the high demand for NMR and x-ray contrast media and the above-mentioned drawbacks of the prior art, there therefore still exists the need for a process for the production of these media, which is suitable above all for the reaction of greater substance amounts. An object of the invention is to provide such a process.

Upon further study of the specification and appended claims, further objects and advantages of this invention will become apparent to those skilled in the art.

These objects are achieved by the inventive process.

It has been found that surprisingly N-β-hydroxyalkyl-tri-N-carboxyalkyl-1,4,7,10-tetraazacyclododecane and N-β-hydroxyalkyl-tri-N-carboxyalkyl-1,4,8,11-tetraazacyclotetradecane derivatives of general formula I

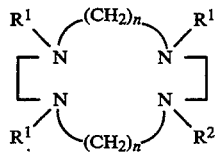 (I)

wherein
R$^1$ is —(CH$_2$)$_{1-6}$—COOY optionally substituted by R$^3$,
R$^3$ is hydrogen, C$_1$-C$_6$-alkyl, benzyl, benzyloxyalkyl or phenyl,
Y is, in each case, hydrogen or a metal ion equivalent of an element of atomic numbers 21–29, 31, 32, 37–39, 42–44, 49 or 57–83,

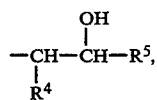

n is, in each case, 2 or 3,
R$^4$ R$^5$ independent of one another, are each hydrogen, C$_1$-C$_{20}$-alkyl optionally interrupted by 1 to 10 oxygen atoms, a phenylene, phenylenoxy or phenylenedioxy group, which optionally is substituted by 1 to 3 C$_1$-C$_6$-alkyl, 1 to 3 trifluoromethyl, 1 to 7 hydroxy, 1 to 3 C$_1$-C$_7$-alkoxy, 1 to 3 C$_7$-C$_{10}$-aralkoxy, 1 to 2 CO$_2$R$^6$ radicals, and/or 1 to 2 phenoxy or phenyl groups optionally substituted by 1 to 2 chloro, bromo, nitro or C$_1$-C$_6$-alkoxy radicals,
R$^6$ is hydrogen, C$_1$-C$_6$-alkyl, C$_6$-C$_{10}$-aryl, or C$_6$-C$_{10}$—Ar(C$_1$-C$_4$)alkyl, and
the optionally present hydroxy radicals or carboxy groups optionally are present in protected form,
can be obtained by reacting 1,4,7,10-tetraazacyclododecane or 1,4,8,11-tetraazacyclotetradecane, optionally in the form of their salts, in the presence of a base with an epoxide of formula II

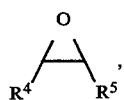 (II)

wherein
R$^4$ and R$^5$ have the above-indicated meanings, and optionally present hydroxy or carboxy groups are optionally protected, in a polar solvent or without solvent at temperatures of about 0° C.–220° C., preferably room temperature e.g., about 20° C.) to 200° C., especially 50° C. to 150°C., within about 0.5–48 hours,
the impurities are separated, optionally, if necessary after adding acids, the resultant product is isolated, and reacted, optionally in the presence of a base, with a compound of formula III

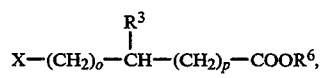 (III)

wherein
R$^3$ and R$^6$ have the above-indicated meanings,
X is a leaving group, and
o and p, independent of one another, are each a number 0 to 5, wherein the sum o+p is less than 6,
optionally after protection of hydroxy or carboxy groups in R$^2$, in a polar solvent at about −10° C. to 170° C. within about 1–100 hours,
protecting groups are optionally cleaved, the thus obtained product of formula I, in which each Y is hydrogen, is then optionally reacted in a way known in the art with at least one metal oxide or metal salt of an element of atomic numbers 21–29, 31, 32, 37–39, 42–44, 49 or 57–83, and,
if desired, still present acidic hydrogen atoms are substituted by cations of inorganic and/or organic bases, amino acids or amino acid amides, or the corresponding acid groups are converted, completely or partially, to esters or amides. The thus obtained complex can then be isolated.

The process according to the invention is distinguished with respect to the prior art by several decisive advantages:

1) The use of nitrogen protecting groups is completely avoided;
2) The tetraazamacrocycles, which carry sensitive groups, such as, e.g., hydroxy groups, can be produced by this process on an industrial scale;
3) The extraction steps, following reaction with the epoxide of formula II, make possible a complete separation of by-products, so that expensive chromatographic separations or selective precipitations are eliminated;
4) The process according to the invention results in a considerably lower number of steps to obtain the tetra-substituted macrocycle than the processes of the prior art; and
5) In the first reaction step, at most one equivalent macrocycle is used relative to epoxide and the substitution product is obtained in high yields; thus, a greater loss of the very expensive starting material 1,4,7,10-tetraazacyclododecane is avoided.

The R$^1$ carboxyalkyl group can be unbranched or branched, and unbranched carboxyalkyl groups are preferred. The length of the alkyl chain can be 1 to 6 carbon atoms, preferably 1 to 2 carbon atoms.

As alkyl groups for R$^6$ and R$^3$ with 1–6 carbon atoms, straight-chain or branched alkyl groups are suitable, such as, for example, methyl, ethyl, propyl, isopropyl, butyl, isobutyl, and tert-butyl. Methyl, ethyl, and tert-butyl are especially preferred.

Preferred radicals for R$^4$ and R$^5$ are hydrogen, methyl, ethyl, hydroxymethyl, 2-hydroxyethyl, 2-hydroxy-1-(hydroxymethyl)ethyl, 1-(hydroxymethyl)ethyl, propyl, isopropyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-hydroxy-2-methylbutyl, 3-hydroxy-2-methylbutyl, 4-hydroxy-2-methylbutyl, 2-hydroxyisobutyl, 3-hydroxyisobutyl, 2,3,4-trihydroxybutyl, 1,2,4-trihydroxybutyl, pentyl, cyclopentyl, 2-methoxyethyl, hexyl, decyl, tetradecyl, triethylene glycol methyl ether, tetraethylene glycol methyl ether and methoxybenzyl as well as the
—CH$_2$—O—C$_{11}$H$_{22}$—OH,
—CH$_2$—O—C$_6$H$_4$—O—(CH$_2$CH$_2$O)$_2$—CH$_3$,
—CH$_2$—O—C$_6$H$_4$—O—(CH$_2$CH$_2$O)$_3$—C$_5$H$_{11}$,
—CH$_2$—O—C$_6$H$_4$—O—C$_4$H$_8$—OH, —(CH₂CH₂O)₅—CH₃,
—C₉H₁₈—COOH,
—C₉H₁₈—OH,
—CH₂—O—C₆H₄—O—C₆H₁₂—COOH,
—CH₂—O—C₆H₄—O—C₄H₈—O—CH₂—CHOH—CH₂OH,
—(CH₂CH₂O)₃—C₅H₁₁,
—CH₂—O—C₁₀H₂₀—COOH,
—CH₂—O—C₆H₄—Cl,
—CH₂—O—C₆H₄—NO₂,
—CH₂—O—C₆H₃Cl₂,
—CH₂—O—C₆H₄—COOH,
—CHOH—CH₂OH,
—CH₂—O—CH₂—CHOH—CH₂OH,
—CH₂—O—C₆H₄—O—CH₂—COOH, and
—CH₂—O—C₆H₄—C₅H₁₁.

Preferably, R⁴ and R⁵ are each, independent of one another, hydrogen, C₁-C₄-alkyl, or C₁-C₄-alkyl substituted by 1-4 hydroxy groups. Especially preferred groups for R⁴ are hydrogen, methyl and hydroxymethyl and for R⁵ are methyl, hydroxymethyl, and 1,2-dihydroxymethyl.

Preferred aryl groups and aralkyl groups R⁶ are phenyl, naphthyl and benzyl.

Especially preferred radicals R⁶ are hydrogen, methyl or benzyl.

Especially preferred radicals R³ are hydrogen, C₁-C₃-alkyl or benzyloxymethyl.

In the epoxide compound of formula II, optionally present carboxyl and/or hydroxy groups are present preferably in protected form.

Acid protecting groups, which can also stand for R⁶, include C₁-C₆-alkyl, C₆-C₁₀-aryl and C₆-C₁₀—Ar(-C₁-C₄)alkyl groups, for example, the methyl, ethyl, propyl, n-butyl, t-butyl, phenyl, and benzyl. Diphenylmethyl, triphenylmethyl, bis (p-nitrophenyl) -methyl group, as well as trialkylsilyl groups, are also suitable acid protecting groups.

The cleavage of the protecting groups takes place according to the processes known to one skilled in the art, for example, by hydrolysis, hydrogenolysis, alkaline saponification of the esters with alkali in aqueous alcoholic solution at temperatures of 0° to 50° C., acid saponification with mineral acids or in the case of, e.g., tert-butyl esters with the help of trifluoroacetic acid.

As hydroxy protecting groups, e.g., the benzyl, 4-methoxybenzyl, 4-nitrobenzyl, trityl, diphenylmethyl, trimethylsilyl, dimethyl-t-butylsilyl, diphenyl-t-butylsilyl groups are suitable.

The hydroxy groups can also be present, e.g., as THP ether, α-alkoxyethyl ether, MEM ether or as esters with aromatic or aliphatic carboxylic acids, such as, e.g., acetic acid or benzoic acid. In the case of polyols, the hydroxy groups can also be protected in the form of ketone acetals with, e.g., acetone, acetaldehyde, cyclohexanone or benzaldehyde.

The hydroxy protecting groups can be released according to the literature methods known to one skilled in the art, e.g., by hydrogenolysis, reductive cleavage with lithium/ammonia, acid treatment of the ethers and ketone acetals or alkali treatment of the esters (see, e.g., "Protective Groups in Organic Synthetics," T. W. Greene, John Wiley and Sons 1981).

Every leaving group familiar to one skilled in the art can stand for leaving group X. For example, acetate, brosylate, mesylate, nosylate, tosylate, trifluoroacetate, trifluorosulfonate, chlorine, bromine or iodine can be mentioned. Preferred leaving groups are chlorine and bromine, especially preferred is chlorine.

As the starting compound, the macrocyclic compounds 1,4,7,10-tetraazacyclododecane or 1,4,8,11-tetraazacyclotetradecane or their salts are used for the process according to the invention.

As salt formers, all inorganic and organic acids are suitable which form stable salts with the above-mentioned macrocycles. For example, phosphoric acid, hydrochloric acid, sulfuric acid or p-toluenesulfonic acid can be mentioned.

In a preferred process, the above-mentioned macrocycles are used as hydrochlorides or as sulfates. These can be obtained according to processes known in the literature. The sulfate can be obtained, e.g., according to Organic Synthesis, Vol. 58, 89, 1978. But it is designated as "polyhydrosulfate" in the literature, whose content has to be determined by sulfur determination after each batch. The content fluctuates between 3 and 4 equivalents of sulfuric acid.

The tetrahydrochloride can be obtained according to J. Amer. Chem. Soc., 96, 2268, (1974) or according to Recueil des Traveaux de Pays Bas [Collection of Works of the Netherlands], 110, 124, (1991).

The molar ratio of macrocycle to epoxide is preferably 1:1 to 1:2 according to the process of the invention, and an excess of epoxide is especially preferred (e.g., 1:1.2, 1:1.4 or 1:1.5).

The base added in the reaction of the macrocycle with the epoxide of formula II

can be one of the usual inorganic or organic bases known to one skilled in the art such as, for example, potassium hydroxide, sodium hydroxide, lithium hydroxide, barium hydroxide, calcium hydroxide, pyridine or N,N-dimethylaminopyridine. Potassium hydroxide, sodium hydroxide, lithium hydroxide are preferably used, sodium hydroxide is especially preferably used.

If the reaction is to be performed without solvent, the free macrocyclic compound has to be reacted. The latter can be obtained, e.g., analogously to Helv. Chim. Acta, 66, 863 (1983) from the sulfate by base treatment.

As solvents, polar aprotic solvents, such as, e.g., acetonitrile, diethyl carbonate, diethyl ether, dimethylacetamide, dimethyl sulfoxide, dioxane, N-methylpyrrolidone, tetrahydrofuran or tetramethylurea and their mixtures as well as protic solvents, such as, for example, alcohols with 1-8 C atoms, are suitable. Methanol, ethanol, propanol, isopropanol, n-butanol, isobutanol, tert-butanol, for example, can be mentioned.

If the solvents used for this reaction are water-miscible, they are removed by distillation after the end of the reaction before an extraction.

With sufficient solubility of the reactants, relatively nonpolar aprotic solvents, such as, for example, benzene, toluene or hydrocarbons, such as, for example, n-hexane, can also be used for the reactions.

The reaction with the epoxide of formula II is performed at temperatures between 0°–220° C., preferably between room temperature and 200° C., especially preferably between 50° C. and 150° C. The reaction time in each corresponding temperature interval is 1 to 48 (e.g., 5 to 48), preferably 1 to 24 (e.g., 5 to 24), especially preferably 1 to 6, hours.

The purification of the monoalkylation product performed after the end of the reaction can take place, e.g., by extraction, optionally in several stages.

It is an advantage of the process according to the invention that the isolation of the monoalkylation product is not necessary.

But if the cleavage of protecting groups and/or an isolation of the monoalkylation product is desired, it advantageous to add mineral acids or organic acids, such as, for example, hydrochloric acid, sulfuric acid, formic acid, acetic acid or trifluoroacetic acid.

The following reaction to introduce the three carboxyalkyl groups takes place by reaction with a compound of general formula III

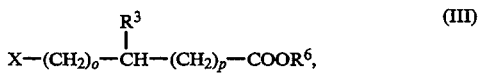

in polar solvents, such as, for example, acetonitrile, acetone, dimethylformamide, dimethyl sulfoxide, hexamethylphosphoric acid triamide, tetrahydrofuran or water or in alcohols with a chain length with up to 8 C atoms, as they have already been described for the first reaction. Dimethylformamide and water are preferred.

The reaction is performed at temperatures of $-10°$ C.-170° C., preferably at 0°-120° C., especially preferably at 40°-100° C.

The reaction time is about 1–100 hours, preferably 1–30 hours, especially preferably 3–12 hours.

In an especially preferred process, the compound of formula III is chloroacetic acid.

The bases added as acid traps in the reaction with the compound of formula III can be tertiary amines (for example, triethylamine, trimethylamine, N,N-dimethylaminopyridine, 1,5-diazabicyclo[4.3.0]-nonene-5(DBN), 1,5-diazabicyclo[5.4.0]-undecene-5-(DBU)), alkali or alkaline-earth carbonates, bicarbonates or hydroxides (for example, lithium, sodium potassium, magnesium, calcium, barium, -carbonate, -hydroxide and -bicarbonate). Sodium hydroxide is especially preferably used.

The optionally necessary introduction or cleavage of protecting groups of the carboxyl or hydroxy functions takes place according to the methods already mentioned for the first process step.

The production of the metal complexes according to the invention takes place in the way as it has been disclosed in German laid-open specification 34 01 052, by the metal oxide or a metal salt (for example, the nitrate, acetate, carbonate, chloride or sulfate) of the element of atomic numbers 21–29, 31, 32, 37–39, 42–44, 49 or 57–83 being dissolved or suspended in water and/or a lower alcohol (such as, methanol, ethanol or isopropanol) and reacted with the solution or suspension of the equivalent amount of the complexing ligand and then, if desired, present acidic hydrogen atoms being substituted by cations of inorganic and/or organic bases or amino acids.

The introduction of the desired metal ions can take place in this connection both before and after the cleavage of the protecting groups for the optionally present hydroxy or other functional groups.

The neutralization of optionally still present free carboxy groups takes place with the help of inorganic bases (for example, hydroxides, carbonates or bicarbonates) of, for example, lithium, sodium, potassium, magnesium or calcium and/or organic bases, such as, i.a., primary, secondary and tertiary amines, such as, for example, ethanolamine, morpholine, glucamine, N-methylamine and N,N-dimethylamine, as well as basic amino acids, such as, for example, lysine, arginine and ornithine or of amides of originally neutral or acid amino acids.

For the production of neutral complex compounds, enough of the desired bases can be added, for example, to the acid complex salts in aqueous solution or suspension that the point of neutrality is reached. The obtained solution can then be evaporated to dryness in a vacuum. Often, it is advantageous to precipitate the formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others and thus to obtain crystallizates that are easy to isolate and easy to purify. It has proven especially advantageous to add the desired base already during the complexing of the reaction mixture and thus to save a process step.

If the acid complex compounds contain several free acidic groups, it is often suitable to produce neutral mixed salts, which contain both inorganic and organic cations as counterions.

This can happen, for example, by the complexing ligands being reacted in aqueous suspension or solution with the oxide or salt of the element yielding the metal ion and half of the amount of an organic base necessary for neutralization, the formed complex salt being isolated, it being optionally purified and then mixed with the necessary amount of inorganic base for complete neutralization. The sequence of the addition of base can also be reversed.

Another possibility, to achieve neutral complex compounds, consists in converting the remaining acid groups in the complex completely or partially into, for example, esters or amides. This can happen by additional reaction on the completed complex (for example, by exhaustive reaction of the free carboxy groups with dimethyl sulfate). If the remaining acid groups are converted only partially to esters or amides, the free acid groups then still remaining can be converted to their salts as described above.

The following embodiments are used to explain this invention, but they are not to limit it.

For the ion exchange chromatography, various embodiments of the product Amberlite ® of the Rohm & Haas company are used.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications cited above and of corresponding German application P 42 18 744.3, are hereby incorporated by reference.

EXAMPLES

Example 1

Example 1a 10-(1-Hydroxymethyl-2,3-dihydroxypropyl-1,4,7,10-tetraazacyclododecane tetrahydrochloride 120 g (3 mol) of sodium hydroxide is added under nitrogen atmosphere to 282.3 g (500 mmol) of 1,4,7,10-tetraazacyclododecanetetrasulfate in 1200 ml of n-butanol. The mixture is heated and resulting water is azeotropically distilled off. Then, 86.5 g (600 mmol) of 4,4-dimethyl-3,5,8-trioxabicyclo[5,1,0]-octane in 200 ml of butanol is instilled. The reaction solution is refluxed for two hours and mixed again with 21.6 g (150 mmol) of 4,4-dimethyl-3,5,8-trioxabicyclo[5,1,0]-octane. After another two hours of reflux, it is cooled to room temperature. The reaction mixture is mixed with 1000 ml of water and stirred for 30 minutes. The phases are separated. The butanol phase is mixed with 250 ml of concentrated hydrochloric acid, stirred for one hour at 70° C. and concentrated by evaporation in a vacuum to 200 ml. 1000 ml of absolute methanol is added. After concentration by evaporation, 500 ml of absolute methanol is again added. The solution is cooled in ice/water, and the precipitating crystals are suctioned off. The crystals are washed once with butanol and twice with methyl-tert-butyl ether (MTB ether) and dried. The product loses HCl with drying. 200.5 g (95% of theory) of 10-(1-hydroxymethyl-2,3-dihydroxypropyl)-1,4,7,10-tetraazacyclododecane tetrahydrochloride is obtained as white crystals.

Melting point: 214°–216° C.

Elementary analysis: Cld: C 34.13 H 7.64 N 13.27 Cl 33.59 Fnd: C 35.19 H 7.85 N 13.67 Cl 29.61

Example 1b 10-(1-Hydroxymethyl-2,3-dihydroxypropyl)-1,4,7-triscarboxymethyl-1,4,7,10-tetraazacyclododecane 105.5 g (250 mmol) of the compound obtained in example 1a is dissolved in 422 ml of water and mixed with 118.1 g (1.25 mol) of chloroacetic acid. It is adjusted to pH=10 with potassium hydroxide. The reaction solution is stirred at 70° C. for four hours and the pH is maintained at 9–10. Then, after adding 23.6 g of chloroacetic acid, it is stirred for another twelve hours under these conditions. After cooling to room temperature, it is acidified with concentrated hydrochloric acid to pH=0.8. The solution is evaporated to dryness, the residue is mixed with 400 ml of a mixture of methanol-/ethanol 1:1 and again concentrated by evaporation. After repeating this process, the residue is mixed with 1000 ml of methanol, stirred for 90 minutes at 50° C. and cooled to 0° C. The precipitating potassium chloride is washed twice with methanol. The combined filtrates are evaporated to dryness in a vacuum. 176 g of crude product is obtained. This is dissolved in 200 ml of deionized water and added on a column with 2.7 l of Amberlite ® AMB 252c. The column is washed with deionized water until conductivity can no longer be detected in the eluate. Then, the product is eluted with water/ammonia. Fractions containing the product are combined and evaporated to dryness. 118 g (=105.6 g of product without water, 93% of theory) of 10-(1-hydroxymethyl-2,3-dihydroxypropyl)-1,4,7-triscarboxymethyl-1,4,7,10-tetraazacyclododecane is obtained.

Elementary analysis: Cld: C 47.98 H 7.61 N 12.43 (corrected for water) Fnd: C 47.35 H 7.63 N 12.32

Water content: 10.51%

Example 1c

Gadolinium complex of 10-(1-hydroxymethyl-2,3-dihydroxypropyl)-1,4,7-triscarboxymethyl-1,4,7,10-tetraazacyclododecane 118 g of the compound obtained from example 1b is dissolved in 530 ml of deionized water and mixed with 44.5 g (123 mmol) of gadolinium oxide. The solution is heated for two hours to 95° C., cooled and stirred for one hour at room temperature with 30 ml of acid ion exchanger (Amberlite ® IR 120) and 30 ml of basic ion exchanger (Amberlite ® IRA 67) each. Then, the solution is filtered and the filtrate is briefly boiled up with activated carbon. After renewed filtration, it is concentrated by evaporation and recrystallized from ethanol/water.

105 g (74% of theory) of the gadolinium complex of 10-(1-hydroxymethyl-2,3-dihydroxypropyl)-1,4,7-triscarboxymethyl-1,4,7,10-tetraazacyclododecane is obtained.

Melting point: >300° C.

Elementary analysis: Cld: C 35.75 H 5.17 N 9.27 Gd 26.00 Fnd: C 35.63 H 5.15 N 9.25 Gd 25.97

Example 2

Example 2a 10-(1-Hydroxymethyl-2,3-dihydroxypropyl)-1,4,7-triscarboxymethyl-1,4,7,10-tetraazacyclododecane 68 g (1.7 mol) of sodium hydroxide is added to 141.1 g (250 mmol) of 1,4,7,10-tetraazacyclododecanetetrasulfate in 600 ml of n-butanol. The mixture is heated and water is azeotropically distilled off. Then, 55.0 g (382 mmol) of 4,4-dimethyl-3,5,8-trioxabicyclo-[5,1,0]-octane is instilled. After completion of the addition, it is refluxed for one hour. Then, it is cooled to room temperature, mixed with 500 ml of water and stirred for 30 minutes. The phases are separated and the butanol phase is evaporated to dryness. The residue is taken up in 600 ml of water and extracted three times with ethyl acetate. The water phase is mixed with 95 g of chloroacetic acid and brought to pH 10. After adding 159 g of $Na_2CO_3$, it is heated to 80° C. and stirred for four hours. Then, 20 g of chloroacetic acid is added, and it is stirred for another twelve hours at 80° C. The reaction mixture is cooled to room temperature, adjusted to pH 0.8 with concentrated hydrochloric acid, heated to 60° C. and stirred for one more hour. Then, it is evaporated to dryness, mixed with 400 ml of a mixture of methanol/ethanol 1:1 and again concentrated by evaporation. This process is repeated, the residue is taken up in 1000 ml of methanol, stirred for 90 minutes at 50° C. and cooled to 0° C. The precipitating potassium chloride is suctioned off and washed twice with methanol. The combined filtrates are evaporated to dryness in a vacuum. The yield of crude product is 176 g. It is now dissolved in 200 ml of deionized water and added on a column with 2.7 l of Amberlite ® AMB 252c. The column is washed with deionized water until conductivity is no longer to be detected in the eluate. Then, the product is eluted with water/ammonia. The substance-containing fractions are combined and evaporated to dryness. 105 g (93% of theory) of 10-(1-hydroxymethyl-2,3-dihydroxy-propyl)-1,4,7-triscarboxymethyl-1,4,7,10-tetraazacyclododecane is obtained.

Elementary analysis: Cld: C 47.98 H 7.61 N 12.43 (corrected for water) Fnd: C 47.15 H 7.72 N 12.39

Water content: 9.5%

Example 2b

Gadolinium complex of 10-(1-hydroxymethyl-2,3-dihydroxypropyl)-1,4,7-triscarboxymethyl-1,4,7,10-tetraazacyclododecane 105 g of the compound obtained under example 2a is dissolved in 500 ml of deionized water and mixed with 40.5 g of gadolinium oxide. Then, the reaction is performed as described under example 1c. 109 g (72% of theory) of the gadolinium complex of 10-(1-hydroxymethyl-2,3-dihydroxypropyl)- 1,4,7-triscarboxymethyl-1,4,7,10-tetraazacyclododecane is obtained.

Melting point: >300° C.

Elementary analysis: Cld: C 35.75 H 5.17 N 9.27 Gd 26.00 Fnd: C 35.59 H 5.11 N 9.28 Gd 25.98

Example 3

Example 3a 10-(6-Hydroxy-2,2-dimethyl-1,3-dioxepan-5-yl)-1,4,7,10-tetraazacyclododecane 56.1 g (1.4 mol) of sodium hydroxide is added to 124.0 g (250 mmol) of tetraazacyclododecanesulfate in 600 ml of n-butanol. The mixture is heated and resulting water is azeotropically distilled off. Then, 43.25 g (300 mmol) of 4,4-dimethyl-3,5,8-trioxabicyclo[5,1,0]-octane in 100 ml of butanol is added. The reaction mixture is refluxed for one hour and mixed again with 8.25 g of sodium hydroxide. Resulting water is distilled off and then mixed again with 7.2 g of 4,4-dimethyl-3,5,8-trioxabicyclo[5,1,0]-octane. After 30 minutes of refluxing, it is cooled to 50° C. and mixed with 400 ml of deionized water. After 15 minutes at 40° C., the first water phase is separated. The butanol phase is mixed with 300 ml of water and 3.75 ml of glacial acetic acid and stirred for 15 more minutes. Then, the second water phase is separated. Then, the butanol phase is extracted twice with 200 ml of water and 3.75 ml of glacial acetic acid each and absorptively precipitated once with 200 ml of water. Water phases 2-5 are combined, mixed with 12.5 ml of 50% sodium hydroxide solution and shaken out twice with 150 ml each and twice with 100 ml of butanol each. The combined washing butanol phases are washed twice with 100 ml of water each. All the butanol phases are combined and mixed with 300 ml of water. 12.75 ml of glacial acetic acid is instilled with stirring. After 30 minutes of stirring, the water phase is separated. The butanol phase is extracted twice more with 200 ml of water each. The combined three water phases are washed twice with 100 ml of methylene chloride each. A sample of about 100 ml is drawn, whose content is determined on HPLC against external standards, and the water content of the dried sample is determined. 61.3 g (72% of theory) of 10-(6-hydroxy-2,2-dimethyl-1,3-dioxepan-5-yl)-1,4,7,10-tetraazacyclododecane is obtained.

Water content: 4.8%

Example 3b 10-(1-Hydroxymethyl-2,3-dihydroxypropyl)-1,4,7-triscarboxymethyl-1,4,7,10-tetraazacyclododecane 72.7 g (767 mmol) of chloroacetic acid is added under ice/water cooling and nitrogen atmosphere to 60.7 g (192 mmol) of the crude product obtained from example 3a in 500 ml of deionized water. Then, the pH is adjusted to 9.5 with about 42 ml of 10 molar sodium hydroxide solution. The reaction solution is heated to 70° C. and the pH is kept at 9.1-9.5 by adding 10 molar sodium hydroxide solution. For 4 hours of additional stirring time, the pH is maintained at 70° C. The reaction mixture is cooled to 30° C. and acidified with 97 ml of conc. HCl to pH=0.8, heated to 60° C. and stirred for one more hour at this temperature. Then, it is evaporated to dryness in a vacuum at this temperature. The residue is mixed twice with 310 ml of MeOH/EtOH each and in each case again evaporated to dryness. The residue is then mixed with 620 ml of methanol and stirred at 50° C. for 30 minutes, cooled in ice/water and suctioned off, NaCl residue is rewashed with ice-cold methanol. The filtrate is evaporated to dryness in a vacuum. The thus obtained crude product is dissolved in 133 ml of deionized water, added on a column (2.0 l of Amberlite® AMB 252c). The column is washed with deionized water until a conductivity of 23 μS is detected in the eluate. Then, the product is eluted with water/NH$_3$. The fractions containing product are combined and evaporated to dryness. 68.2 g (78% of theory) of 10-(1-hydroxymethyl- 2,3-dihydroxypropyl)-1,4,7,10-tetraazacyclododecane is obtained.

Elementary analysis: Cld: C 47.98 H 7.61 N 12.43 Fnd: C 47.63 H 7.93 N 12.57

Example 3c

Gadolinium complex of 10-(1-hydroxymethyl-2,3-dihydroxypropyl)-1,4,7-triscarboxymethyl-1,4,7,10-tetraazacyclododecane 68.0 g of the compound obtained from example 3b is dissolved in 306 ml of deionized water, mixed with 24.65 g (68.1 mmol) of gadolinium oxide and heated to 95° C. After 45 minutes at this temperature, 2.74 g of gadolinium oxide is added, stirred again for 75 minutes at 95° C., 2.04 g of activated carbon is added and hot filtered. The filtrate is purified on ion exchanger as in example 1c and crystallized from water/ethanol. 71.8 g (78% of theory) of the gadolinium complex of 10-(1-hydroxymethyl-2,3-dihydroxypropyl)-1,4,7-triscarboxymethyl-1,4,7,10-tetraazacyclododecane is obtained.

Elementary analysis: Cld: C 35.75 H 5.17 N 9.27 Gd 26.00 Fnd: C 35.67 H 5.19 N 9.27 Gd 25.99

Example 4

Example 4a 10-(2-Hydroxypropyl)-1,4,7,10-tetraazacyclododecane tetrahydrochloride 141.1 g (250 mmol) of 1,4,7,10-tetraazacyclododecanetetrasulfate is dissolved in 600 ml of n-butanol and mixed under nitrogen atmosphere with 68 g of sodium hydroxide. The mixture is heated and water is azeotropically distilled off. Then, 20.0 g (350 mmol) of propylene oxide is instilled, and after completion of the addition, it is boiled for one hour. Then, it is cooled to room temperature, mixed with 500 ml of water and stirred for 30 more minutes. The phases are separated and the butanol phase is mixed with 125 ml of concentrated hydrochloric acid. The mixture is heated to 70° C., stirred for one more hour and concentrated by evaporation in a vacuum to 100 ml. 500 ml of absolute methanol is added. After repeating the concentration by evaporation, 200 ml of n-butanol is added, and the mixture is cooled in ice/water. The precipitating crystals are suctioned off and washed twice with methyl-tert-butyl ether. After drying (the product in this case loses HCl), 70.5 g (75% of theory) of white crystalline product is obtained.

Melting point: 221°–224° C. (decomposition)

Elementary analysis: Cld: C 35.12 H 8.04 N 14.89 Cl 37.69 Fnd: C 37.23 H 8.36 N 15.68 Cl 32.61

Example 4b 10-(2-Hydroxypropyl)-1,4,7-triscarboxymethyl-1,4,7,10-tetraazacyclododecane 53 g (125 mmol) of the compound obtained in example 4a is reacted analogously to example 1b. 56.5 g (90% of theory) of 10-(2-hydroxypropyl)-1,4,7-triscarboxymethyl-1,4,7,10-tetraazacyclododecane is obtained.

Elementary analysis: Cld: C 50.48 H 7.98 N 13.85 (corrected on water) Fnd: C 50.13 H 8.14 N 14.13
Water content: 10.1%

Example 5

Example 5a 10-(1-Hydroxymethyl-2,3-dihydroxypropyl)-1,4,7,10-tetraazacyclododecane tetrahydrochloride Analogously to example 1a, starting from 192 g (500 mmol) of 1,4,7,10-tetraazacyclododecane tetrahydrochloride, 183 g (71% of theory) of 10-(1-hydroxymethyl-2,3-dihydroxypropyl)-1,4,7,10-tetraazacyclododecane tetrahydrochloride is obtained.

Melting point: 213°–215° C. (decomposition)

Example 5b 10-(1-Hydroxymethyl-2,3-dihydroxypropyl)-1,4,7-triscarboxymethyl-1,4,7,10-tetraazacyclododecane Analogously to example 1b, starting from 105.5 g (250 mmol) of the compound obtained from example 5a, 110 g (97% of theory) of 10-(1-hydroxymethyl-2,3-dihydroxypropyl)-1,4,7-triscarboxymethyl-1,4,7,10-tetraazacyclododecane is obtained.

Elementary analysis: Cld: C 47.98 H 7.61 N 12.43 Fnd: C 47.38 H 7.62 N 12.37

Example 5c

Gadolinium complex of 10-(1-hydroxymethyl-2,3-dihydroxypropyl)-1,4,7-triscarboxymethyl-1,4,7,10-tetraazacyclododecane Analogously to example 1c, 98 g (66% of theory) of the gadolinium complex of 10-(1-hydroxymethyl-2,3-dihydroxypropyl)-1,4,7-triscarboxymethyl-1,4,7,10-tetraazacyclododecane is obtained from 110 g of the compound obtained from example 5b.

Melting point: >300° C.

Example 6

10-(6-Hydroxy-2,2-dimethyl-1,3-dioxepan-5-yl)-1,4,7,10-tetraazacyclododecane 121.5 g (250 mmol) of 1,4,7,10-tetraazacyclododecanesulfate (×3.2 H$_2$SO$_4$) is suspended in 500 ml of n-butanol and mixed with 48 g (1.2 mol) of sodium hydroxide. The mixture is heated slowly and the resulting water is azeotropically distilled off. A solution of 4,4-dimethyl-3,5,8-trioxabicyclo-[5,1,0]-octane is added in the corresponding amount of n-butanol also distilled off in the distillation. Then, it is refluxed for two hours. The mixture is cooled and mixed with 300 ml of water. The butanol phase is separated and concentrated by evaporation. The residue is mixed with 100 ml of water and again concentrated by evaporation. This process is repeated. 135.1 g of crude product is obtained, which is dissolved in 600 ml of water and washed with ethyl acetate. The combined ethyl acetate phases are back-washed with water. All water phases are combined and concentrated by evaporation. 117.0 g of 10-(6-hydroxy-2,2-dimethyl-3-dioxepan-5-yl)-1,4,7,10-tetraazacyclodecane is obtained as crude product. The additional reaction takes place as described in example 3.

Example 7

Example 7a 10-(6-Hydroxy-2,2-dimethyl-1,3-dioxepan-5-yl)-1,4,7,10-tetraazacyclododecane 10 kg of 1,4,7,10-tetraazacyclododecanesulfate (×3.2 H$_2$SO$_4$) is introduced together with 4 kg of sodium hydroxide in pellets and 40 l of n-butanol is pumped into it. With stirring and under nitrogen atmosphere, it is heated and resulting water is azeotropically distilled off. Then, a solution of 3.6 kg of 4,4-dimethyl-3,5,8-trioxabicyclo-[5,1,0]-octane in 20 l of n-butanol is added and refluxed for one hour with stirring and under nitrogen atmosphere. Then, 7 l of n-butanol is again distilled off and 0.6 kg of 4,4-dimethyl-3,5,8-trioxabicyclo[5,1,0]-octane is added. After a half hour of refluxing with stirring and under nitrogen atmosphere, it is cooled to a 40° C. internal temperature, mixed with 40 l of deionized water. The phases are separated and the organic phase is mixed with 300 ml of glacial acetic acid and 10 l of deionized water. After 20 minutes, the phases are again separated. The aqueous phase is mixed with 100 ml of 50% sodium hydroxide solution and 10 l of n-butanol and allowed to stand for 20 minutes. The phases are separated. The organic phase is combined with that obtained in the preceding separation and concentrated by evaporation to 10 l. Then, 50 l of demineralized water is added and the mixture is reduced to a volume of 45 l. The mixture is cooled to a 20° C. internal temperature and mixed during the latter with 1 l of acetic acid. After adding 10 l of methylene chloride or ethyl acetate, it is stirred for 15 minutes and then allowed to stand for 20 minutes. The phases are separated. The aqueous phase is extracted twice more with 10 l of methylene chloride each. All methylene chloride phases are combined, stirred with 10 l of demineralized water for 15 minutes and allowed to stand for about 20 minutes. The phases are separated and the organic phase is concentrated by evaporation to about 5 l. The aqueous phase is combined with that obtained in the preceding separation and concentrated by evaporation to 40 l in a vacuum at a 70° C. internal temperature. After cooling to room temperature, the obtained solution is used in the next reaction. The content of product is determined from a sample on HPLC against external standards. The content is 4.22 kg (65% of theory).

Example 7b 10-(1-Hydroxymethyl-2,3-dihydroxypropyl)-1,4,7-triscarboxymethyl-1,4,7,10-tetraazacyclododecane 10 kg of 10-(1-hydroxymethyl-2,3-dihydroxypropyl)-1,4,7,10-tetraazacyclododecane is introduced in aqueous solution as obtained from example 7a and diluted with demineralized water on an overall volume of 80 l. 13.6 kg of chloroacetic acid is added. Then, about 8 l of 50% sodium hydroxide solution is added at a maximum 70° C. internal temperature until at most a pH of pH=10 is reached. The batch is stirred for seven hours at this temperature. The pH is kept constant at pH=9.5. Then, 3.4 kg of chloroacetic acid is again added. It is stirred for another three hours at 70° C. and the pH is kept constant. After completion of the reaction, it is cooled to 50° C. and mixed with about 15 l of concentrated hydrochloric acid, and the internal temperature should not exceed 60° C., until a pH of pH=1 is reached. At this temperature, it is concentrated by evaporation in a vacuum. The residue is mixed with 40 l of methanol, heated and refluxed under nitrogen atmosphere for 30 minutes. The crystallized salts are separated and washed with methanol. The combined filtrates are concentrated by evaporation in a vacuum, mixed with 80 l of deionized water. The substance solution is added on an ion exchanger column (ion exchanger Amberlite® A 252c, volume 165 l) prepared in the usual way and flushed with 10 l of deionized water. In a stirred still head, 600 l of deionized water is mixed with 150 l of 25% ammonia solution. The thus diluted ammonia is added on the ion exchanger columns and the eluate is collected in 50 l fractions. The product-containing fractions are combined and concentrated by evaporation in a vacuum first to 50 l and then at a maximum 50° C. casing temperature. The residue is taken up in 30 l of deionized water. The thus obtained solution is used directly in the next stage. The solvents distilled off in the course of the reaction can be used again for additional reactions.

Example 7c

Gadolinium complex of 10-(1-hydroxymethyl-2,3-dihydroxypropyl)-1,4,7-triscarboxymethyl-1,4,7,10-tetraazacyclododecane The solution obtained from example 7b is introduced and optionally diluted to a volume of 24 l. Then, 2.3 kg of gadolinium oxide is added. The mixture is heated with stirring to 90° C. and the pH is optionally adjusted with about 0.6 l of acetic acid to pH =6-7. Once a solution has resulted (insoluble solids are optionally filtered off), it is stirred for one hour at 90° C. The pH is maintained in the meantime. After completion of the reaction, it is cooled to 20° C. and 0.3 kg of activated carbon is added. It is stirred for one hour at 20° C. and the activated carbon is filtered off. The activated carbon is washed free of substances and the solution is filtered several times. Then, the solution is purified on ion exchangers in a way known to one skilled in the art until conductivity can no longer be noted in the eluate and crystallized from ethanol/water and dried. 5.24 kg (which corresponds to a total yield from all stages of 42% of theory) of the gadolinium complex of 10-(1-hydroxymethyl-2,3-dihydroxypropyl)-1,4,7-triscarboxymethyl-1,4,7,10-tetraazacyclododecane is obtained.

Elementary analysis: Cld: C 35.75 H 5.17 N 9.27 Gd 26.00 Fnd: C 35.69 H 5.21 N 9.25 Gd 25.98

Example 8

Example 8a 10-(2-Hydroxy-(2,2-dimethyl-1-1,3-dioxolan-4-yl)ethyl)-1,4,7,10-tetraazacyclododecane Analogously to example 3a, 124 g (250 mmol) of 1,4,7,10-tetraazacyclododecanesulfate (×3.3 H$_2$SO$_4$) is reacted with a total of 50.45 g (350 mmol) of 2,2-dimethyl-4-(2',3'-epoxy)-propoxy-methyl-1,3-dioxolan. 59.3 g (75% of theory) of 10-(2-hydroxy-(2,2-dimethyl-1,3-dioxolan-4-yl)-ethyl)-1,4,7,10-tetraazacyclododecane, which is immediately further reacted, is obtained.

Example 8b 10-(2,3,4-Trihydroxybutyl)-1,4,7-triscarboxymethyl-1,4,7,10-tetraazacyclododecane 59.3 g of the compound obtained from example 8a is reacted analogously to example 3b. 63.7 g (75% of theory) of 10-(2,3,4-trihydroxybutyl)-1,4,7-triscarboxymethyl-1,4,7,10-tetraazacyclododecane is obtained.

Elementary analysis: Cld: C 47.98 H 7.61 N 12.43 Fnd: C 47.21 H 7.64 N 12.92

Example 8c

Gadolinium complex of 10-(2,3,4-trihydroxybutyl)-1,4,7-triscarboxymethyl-1,4,7,10-tetraazacyclododecane 68.0 g of the compound obtained from example 8b is reacted analogously to example 3c. 89.3 g (97% of theory) of the gadolinium complex of 10-(2,3,4-trihydroxybutyl)-1,4,7-triscarboxymethyl-1,4,7,10-tetraazacyclododecane is obtained.

Elementary analysis: Cld: C 35.75 H 5.17 N 9.27 Gd 26.00 Fnd: C 35.64 H 5.23 N 9.23 Gd 26.02

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for production of a N-$\beta$-hydroxyalkyl-tri-N-carboxyalkyl-1,4,7,10-tetraazacyclododecane or N-$\beta$-hydroxyalkyl-tri-N-carboxyalkyl-1,4,8,11-tetraazacyclotetradecane compound of formula I

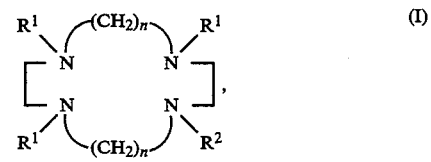

wherein
$R^1$ is —(CH$_2$)$_{1-6}$-COOY optionally substituted by $R^3$;
$R^3$ is hydrogen, C$_1$–C$_6$-alkyl, benzyl, benzyloxyalkyl or phenyl;
Y is, in each case, hydrogen or a metal ion equivalent of an element of atomic numbers 21-29, 31, 32, 37-39, 42-44, 49 or 57-83;

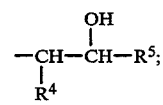

n is, in each case, 2 or 3;
$R^4$ and $R^5$, independent of one another, are each hydrogen, C$_1$–C$_{20}$-alkyl optionally interrupted by 1 to 10 oxygen atoms, a phenylene, phenylenoxy or phenylenedioxy group, which optionally is substituted by 1 to 3 C$_1$–C$_6$-alkyl, 1 to 3 trifluoromethyl, 1 to 7 hydroxy, 1 to 3 C$_1$–C$_7$-alkoxy, 1 to 3 C$_7$–C$_{10}$-aralkoxy, 1 to 2 CO$_2$R$^6$, and/or 1 to 2 phenoxy or phenyl groups optionally substituted by 1 to 2 chloro, bromo, nitro or C$_1$–C$_6$-alkoxy;
$R^6$ is hydrogen, C$_1$–C$_6$-alkyl, C$_6$–C$_{10}$-aryl, or C$_6$–C$_{10}$—Ar(C$_1$–C$_4$)alkyl;
wherein hydroxy or carboxy groups are optionally in protected form;
said process comprising:

reacting 1,4,7,10-tetraazacyclododecane or 1,4,8,11-tetraazacyclotetradecane, optionally in the form of a salt, in the presence of a base, with an epoxide of formula II

wherein
$R^4$ and $R^5$ have the above-indicated meanings and optionally present hydroxy or carboxy groups are optionally protected, in a polar solvent or without solvent, at a temperature of 0° C.–220° C. within 0.5–48 hours;
separating impurities, optionally, if necessary after adding acids;
isolating product;
reacting resultant product, optionally in the presence of a base, with a compound of formula III

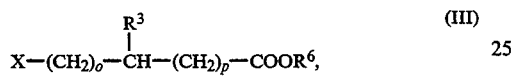

wherein
$R^3$ and $R^6$ have the above-indicated meanings,
X is a leaving group; and
o and p, independent of one another, are each 0–5, and o+p is less than 6;
optionally after protection of hydroxy or carboxy groups in $R^2$ with protecting groups, in a polar solvent at −10° C.–170° C. within 1–100 hours;
optionally cleaving protecting groups; and
the resultant product of formula I, wherein each Y is hydrogen, is optionally reacted with at least one metal oxide or metal salt of an element of atomic numbers 21–29, 31, 32, 37–39, 42–44, 49 or 57–83, and acid hydrogen atoms, optionally, are substituted by cations of inorganic and/or organic bases, amino acids or amino acid amides, or corresponding acid groups, optionally, are converted, completely or partially, to esters or amides.

2. A process according to claim 1, wherein a salt of an inorganic or organic base and 1,4,7,10-tetraazacyclododecane or 1,4,8,11-tetraazacyclotetradecane is employed as the starting material.

3. A process according to claim 2, wherein said starting material is a hydrochloride or sulfate of 1,4,7,10-tetraazacyclododecane or 1,4,8,11-tetraazacyclotetradecane.

4. A process according to claim 3, wherein said starting material is a hydrochloride or sulfate of 1,4,7,10-tetraazacyclododecane.

5. A process according to claim 1, wherein said base used in the reaction with said epoxide of formula II is lithium hydroxide, sodium hydroxide or potassium hydroxide.

6. A process according to claim 1, wherein $R^4$ and $R^5$, are each, independent of one another, hydrogen, $C_1$–$C_4$-alkyl, or $C_1$–$C_4$-alkyl substituted by 1–4 hydroxy.

7. A process according to claim 1, wherein $R^4$ is hydrogen, methyl, or hydroxymethyl and $R^5$ is methyl, hydroxymethyl, or 1,2-dihydroxyethyl.

8. A process according to claim 1, the ratio of epoxide to tetraazamacrocycle is 1:1 to 2:1.

9. A process according to claim 1, wherein the solvent for reaction with said epoxide of formula II is polar or polar and protic.

10. A process according to claim 9, wherein said solvent is n-butanol.

11. A process according to claim 1, wherein reaction with said epoxide of formula II is conducted at a temperature of 20° C.–200° C.

12. A process according to claim 1, wherein reaction with said epoxide of formula II is conducted at a temperature of 50° C.–150° C.

13. A process according to claim 1, wherein $R^3$ is hydrogen, o is 0 and p is 0.

14. A process according to claim 1, wherein the reactions are performed in a one-pot process.

15. A process for production of a N-β-hydroxyalkyl-tri-N-carboxyalkyl-1,4,7,10-tetraazacyclododecane or N-β-hydroxy-alkyl-tri-N-carboxyalkyl-1,4,8,11-tetraazacyclotetradecane compound of formula I

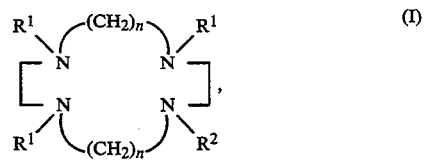

wherein
$R^1$ is —$(CH_2)_{1-6}$—COOY optionally substituted by $R^3$;
$R^3$ is hydrogen, alkyl, benzyl, benzyloxyalkyl or phenyl;
Y is, in each case, hydrogen or a metal ion equivalent of an element of atomic numbers 21–29, 31, 32, 37–39, 42–44, 49 or 57–83;
$R^2$ is

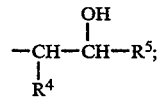

n is, in each case, 2 or 3;
$R^4$ and $R^5$, independent of one another, are each hydrogen, $C_1$–$C_{20}$-alkyl optionally interrupted by 1 to 10 oxygen atoms, a phenylene, phenylenoxy or phenylenedioxy group, which optionally is substituted by 1 to 3 alkyl, 1 to 3 trifluoromethyl, 1 to 7 hydroxy, 1 to 3 alkoxy, 1 to 3 aralkoxy 1 to 2 $CO_2R^6$, and/or 1 to 2 phenoxy or phenyl groups optionally substituted by 1 to 2 chloro, bromo, nitro or alkoxy;
$R^6$ is hydrogen, alkyl, aryl or Ar-alkyl;
wherein hydroxy or carboxy groups are optionally in protected form;
said process comprising:
reacting 1,4,7,10-tetraazacyclododecane or 1,4,8,11-tetraazacyclotetradecane, optionally in the form of a salt, in the presence of a base, with an epoxide of formula II

wherein $R^4$ and $R^5$ have the above-indicated meanings and optionally present hydroxy or carboxy groups are optionally protected, in a polar solvent or without solvent, at a temperature of 0° C.–220° C. within 0.5–48 hours;

separating impurities, optionally, if necessary after adding acids;

isolating product;

reacting resultant product, optionally in the presence of a base, with a compound of formula III

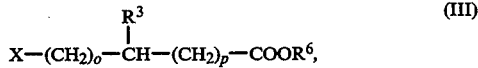

$$X-(CH_2)_o-\overset{R^3}{\underset{|}{CH}}-(CH_2)_p-COOR^6, \quad (III)$$

wherein $R^3$ and $R^6$ have the above-indicated meanings,

X is a leaving group; and o and p, independent of one another, are each 0–5, and o+p is less than 6;

optionally after protection of hydroxy or carboxy groups in $R^2$ with protecting groups, in a polar solvent at −10° C.–170° C. within 1–100 hours;

optionally cleaving protecting groups; and the resultant product of formula I, wherein each Y is hydrogen, is optionally reacted with at least one metal oxide or metal salt of an element of atomic numbers 21–329, 31, 32, 37–39, 42–44, 49 or 57–83, and acid hydrogen atoms, optionally, are substituted by cations of inorganic and/or organic bases, amino acids or amino acid amides, or corresponding acid groups, optionally, are converted, completely or partially, to esters or amides.

16. A process according to claim 1, wherein leaving group X is acetate, brosylate, mesylate, nosylate, tosylate, trifluoroacetate, trifluorosulfonate, chlorine, bromine or iodine;

the hydroxy protecting groups are independently benzyl, 4-methoxybenzyl, 4-nitrobenzyl, trityl, diphenylmethyl, trimethylsilyl, dimethyl-t-butylsilyl, THP ether, α-alkoxyethylether, MEM ether, an ester of an aromatic carboxylic acid, or an ester of an aliphatic carboxylic acid, or, in the case of polyols, hydroxy groups can be protected in the form of a ketone acetal; and the carboxyl protecting groups are independently $C_1$–$C_6$-alkyl, $C_6$–$C_{10}$-aryl, $C_6$–$C_{10}$-Ar($C_1$–$C_4$)-alkyl, diphenylmethyl, triphenylmethyl, bis(p-nitrophenyl)-methyl or a trialkylsilyl group.

* * * * *

UNITED STATES PATENT AND TRADEMARK OFFICE
CERTIFICATE OF CORRECTION

PATENT NO. : 5,386,028
DATED : 01/31/95
INVENTOR(S) : Ulf TILSTAM et al.

It is certified that error appears in the above-indentified patent and that said Letters Patent is hereby corrected as shown below:

Claim 1; column 16, line 50:   Insert -- $R^2$ is -- before formula.

Claim 1; column 16, line 64:   After or delete "$C_6-C_1-$" and insert -- $C_6-C_{10}-$ --.

Claim 1; column 16, line 65:   Delete "O--".

Claim 15; column 20, line 2:   Delete "21-329," and replace with -- 21-29, --.

Signed and Sealed this

Eleventh Day of July, 1995

Attest:

BRUCE LEHMAN

Attesting Officer       Commissioner of Patents and Trademarks